(12) United States Patent
Nelson

(10) Patent No.: US 6,273,090 B1
(45) Date of Patent: Aug. 14, 2001

(54) DEVICE FOR ASSISTING IN READING OF IMAGE SUCH AS MAMMOGRAM AND RELATED METHOD

(76) Inventor: Mary Winn Nelson, 107 Highmount Dr., Greer, SC (US) 29651

(\*) Notice: Subject to any disclaimer, the term of this patent is extended or adjusted under 35 U.S.C. 154(b) by 0 days.

(21) Appl. No.: 09/542,414

(22) Filed: Apr. 4, 2000

(51) Int. Cl.$^7$ ........................................................ A61F 5/37
(52) U.S. Cl. ............................................ 128/846; 128/890
(58) Field of Search .................................... 128/845, 846, 128/890

(56) References Cited

U.S. PATENT DOCUMENTS

| | | | | |
|---|---|---|---|---|
| 4,524,405 | * | 6/1985 | Heard | 362/18 |
| 4,546,757 | * | 10/1985 | Jakahi | 126/438 |

\* cited by examiner

Primary Examiner—Michael A. Brown
(74) Attorney, Agent, or Firm—Dority & Manning, P.A.

(57) ABSTRACT

A device to assist in the reading of an illuminated image is disclosed. The device comprises a blocking member including a plurality of blocking portions pivotally mounted together at a common pivot point so as to be pivotable between a storage position and a use position. Each blocking portion has a distal end, the distal ends of the blocking portions defining a curved edge of the blocking member when the blocking portions are disposed in the use position. The blocking member is at least partially opaque for placement over a portion of the illuminated image to block at least a substantial portion of the illumination light. The curved edge is sized so as to approximate the size and shape of a portion of the illuminated image. The device has particular utility with breast X-ray film and CRT images, including such images where breast implants are present. Two embodiments of the device are disclosed, along with a related method.

22 Claims, 4 Drawing Sheets

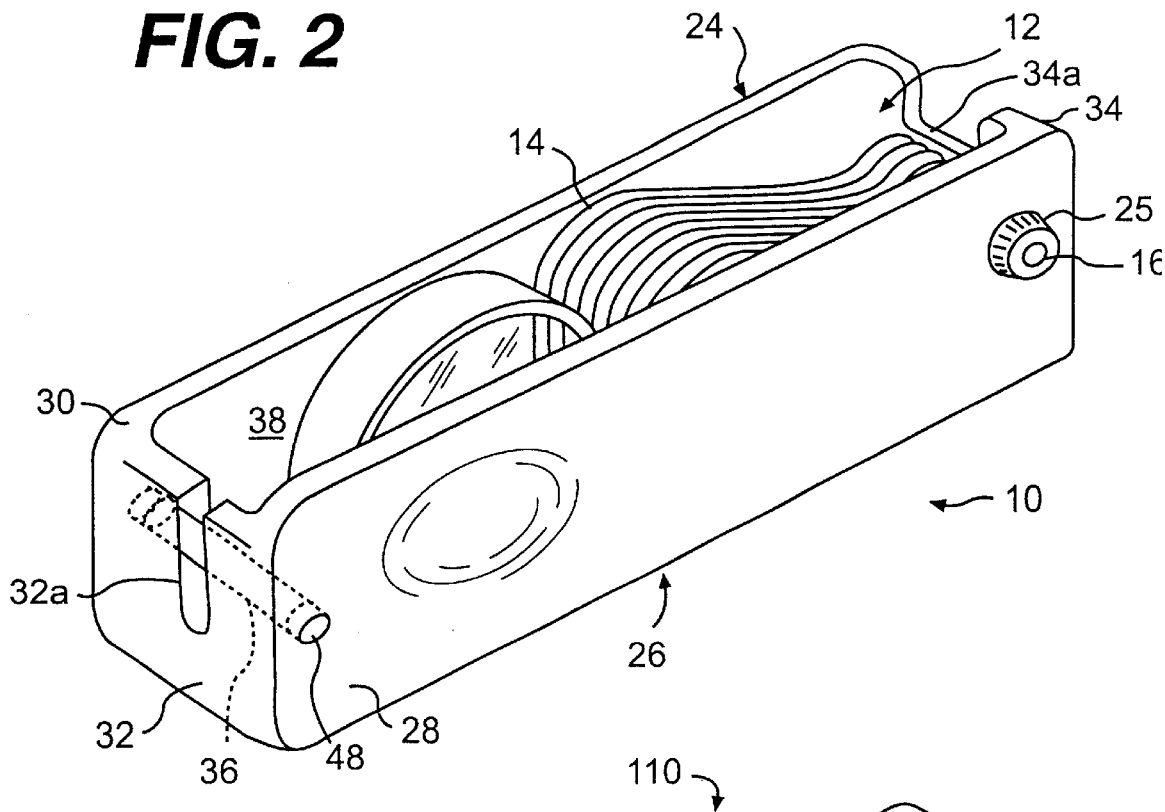
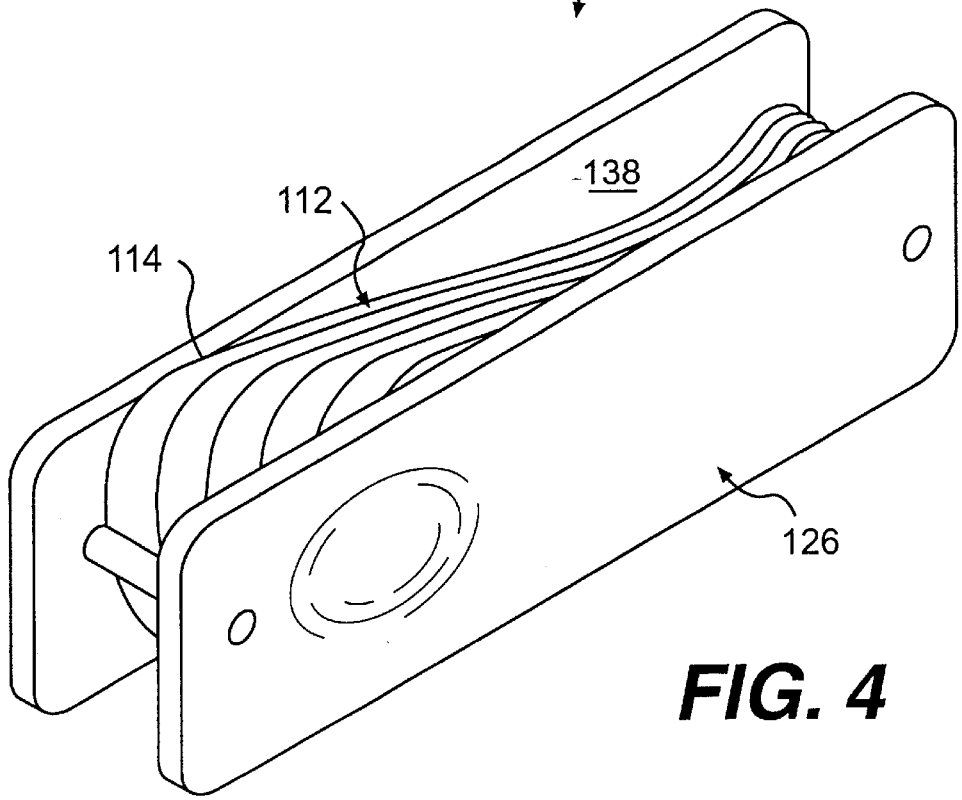

DEVICE FOR ASSISTING IN READING OF IMAGE SUCH AS MAMMOGRAM AND RELATED METHOD

FIELD OF INVENTION

The present invention relates generally to a device to assist in the reading of an illuminated image such as an X-ray film or CRT image of breast tissue, commonly called a mammogram. The present invention more particularly relates to such a device including an adjustably positionable blocking member for blocking for at least a substantial portion of light that passes through the illuminated image to thereby render portions of the image easier to read.

BACKGROUND OF THE INVENTION

In the field of radiology, various devices have been proposed for imaging portions of the human body. For example, magnetic resonance imaging and X-ray devices have been in common use for many years. Specialized mammography X-ray devices have been developed for providing images of breast tissue. Mammography X-ray devices are particularly useful in detecting presence of tumors, microcalcifications, and other abnormalities at an early stage when potentially not yet detectable by touch.

Imaging devices provide output images in various formats, for example via a CRT or printer, or on film. X-ray devices typically provide output in the form of a film that blackens when exposed to X-rays and then developed. Areas of the film exposed to a greater amount of X-ray radiation are blackened more than areas that are exposed to a lesser amount. Different body tissues, bones, etc. block X-ray radiation to differing degrees, and it is the contrast in transmitted radiation impacting the film that provides an image of the exposed body parts.

Exposed X-ray film is typically viewed on an illuminated X-ray viewer that holds the film on a backlit, clear or white surface. Often, the film is mostly black or dark gray, with images appearing in white or light gray. Physicians and mammographers must examine the film very closely to determine whether any small abnormalities such as those mentioned above are present. Very close study of breast X-ray film images is critical, as chances for successful treatment can depend on early detection of tiny abnormalities and corresponding early treatment before the abnormalities grow, multiply, or metastasize. Thus, physicians and mammographers on the lookout for very small features potentially captured by the film often view the brightly illuminated images very closely (within inches of their eyes) or under magnification, or sometimes both. Also, analog or digital images could be displayed on a display element such as a CRT device, rather than on X-ray film. In such situations, a close reading of features in an illuminated image is also required.

The presence of breast implants, whether utilized for reconstructive purposes after surgery such as mastectomy or electively implanted for cosmetic purposes absent such previous surgery, can render reading X-ray images more difficult. For example, breast implants typically block much more radiation than breast tissue. Thus, breast implant images appear almost entirely white or clear on an X-ray viewing device.

Because of the backlighting required to read the X-ray image, and because the studied portion of the image is generally the brighter (whiter) portion of the image, it can be difficult to differentiate between certain features within the X-ray image. Also, viewing such well-lit images may lead to irritation or discomfort simply from having to look closely at illuminated images for an extended period of time.

In situations where implants are present in the images, the bright light passed through the film or displayed on a CRT by the implant portion can render the image even more difficult to properly examine due to the contrast between the bright implant image portions and the typically darker tissue image portions. Also, it can be more difficult to detect abnormalities disposed in tissue adjacent the edges of the implant due to the brightness of the implant image.

OBJECTS AND SUMMARY OF THE INVENTION

Accordingly, it is an object of the present invention to provide a device to assist in the reading of an illuminated image, such as an X-ray film or CRT image of breast tissue, that is simple and effective to use and is inexpensive to produce.

Another object is to provide an advantageous related method of reading such an illuminated image.

In accordance with one aspect of the invention, a device to assist in the reading of an illuminated image of breast tissue is disclosed, the device comprising a blocking member including a plurality of blocking portions pivotally mounted together at a common pivot point so as to be pivotable between a storage position and a use position. Each blocking portion has a distal end, the distal ends of the blocking portions defining a curved edge of the blocking member when the blocking portions are disposed in the use position. The blocking member is at least partially opaque for placement over a portion of the illuminated image to block at least a substantial portion of the illumination light. The curved edge is sized so as to approximate the size and shape of a portion of the illuminated image of the breast tissue.

In one embodiment, at least a portion of the curved edge preferably defines a radius of between about 1 and about 4 inches, and more preferably a radius of between about 2 and about 3 inches. In another embodiment, the curved edge preferably defines a changing radius along the curved edge that ranges from between at least about 1 to at most about 4 inches.

Also, the blocking member preferably includes between 3 and 12 of the blocking portions, and more preferably includes about 8 of the blocking portions.

Optionally, the device may include a gripping member, and the blocking portions may be mounted to the gripping member. The blocking portions may be disposed at least partially within the gripping member for storage.

In accordance with another aspect of the invention, a device to assist in the reading of an illuminated image is disclosed, the device comprising a gripping member and a blocking member including a plurality of blocking portions pivotally attached to the gripping member at a common pivot point so as to be pivotable between a storage position and a use position. Each blocking portion has a distal end, the distal ends of the blocking portions defining a curved edge of the blocking member when the blocking portions are disposed in the use position. The blocking member is at least partially opaque for placement over a portion of the illuminated image to block at least a substantial portion of the illumination light. The curved edge defines a changing radius along the curved edge that ranges from between at least about 1 to at most about 4 inches.

In accordance with yet another aspect of the invention, a method of reading an illuminated image of breast tissue is disclosed, the method comprising illuminating an image of breast tissue, and pivoting a plurality of blocking portions of a blocking member into a use position. The blocking portions are pivotally mounted together at a common pivot point so as to be pivotable between a storage position and the use position. Each blocking portion has a distal end, and the distal ends of the blocking portions define a curved edge of the blocking member when the blocking portions are in the use position. The curved edge is sized so as to approximate the size and shape of a portion of the illuminated image. The method further includes placing the blocking member on a portion of the illuminated image to block at least a substantial portion of the illumination light, and reading the illuminated image.

Other objects and aspects of the invention will be apparent from the following description, claims, and figures, or may be apparent to one skilled in the art based on these disclosures.

BRIEF DESCRIPTION OF THE DRAWINGS

Preferred embodiments of the invention, along with other characteristics, details, and advantages of the invention, are set forth in the descriptions and claims that follow, in which examples of the embodiments of the invention are explained through the attached drawings. In the drawings:

FIG. 2 is a perspective view of the device of FIG. 1 showing the blocking member in a storage position within the gripping member;

FIG. 4 is a perspective view of the device of FIG. 3 with the blocking member retracted into a storage position within a gripping member;

DESCRIPTION OF THE PREFERRED EMBODIMENTS

Figure 1:
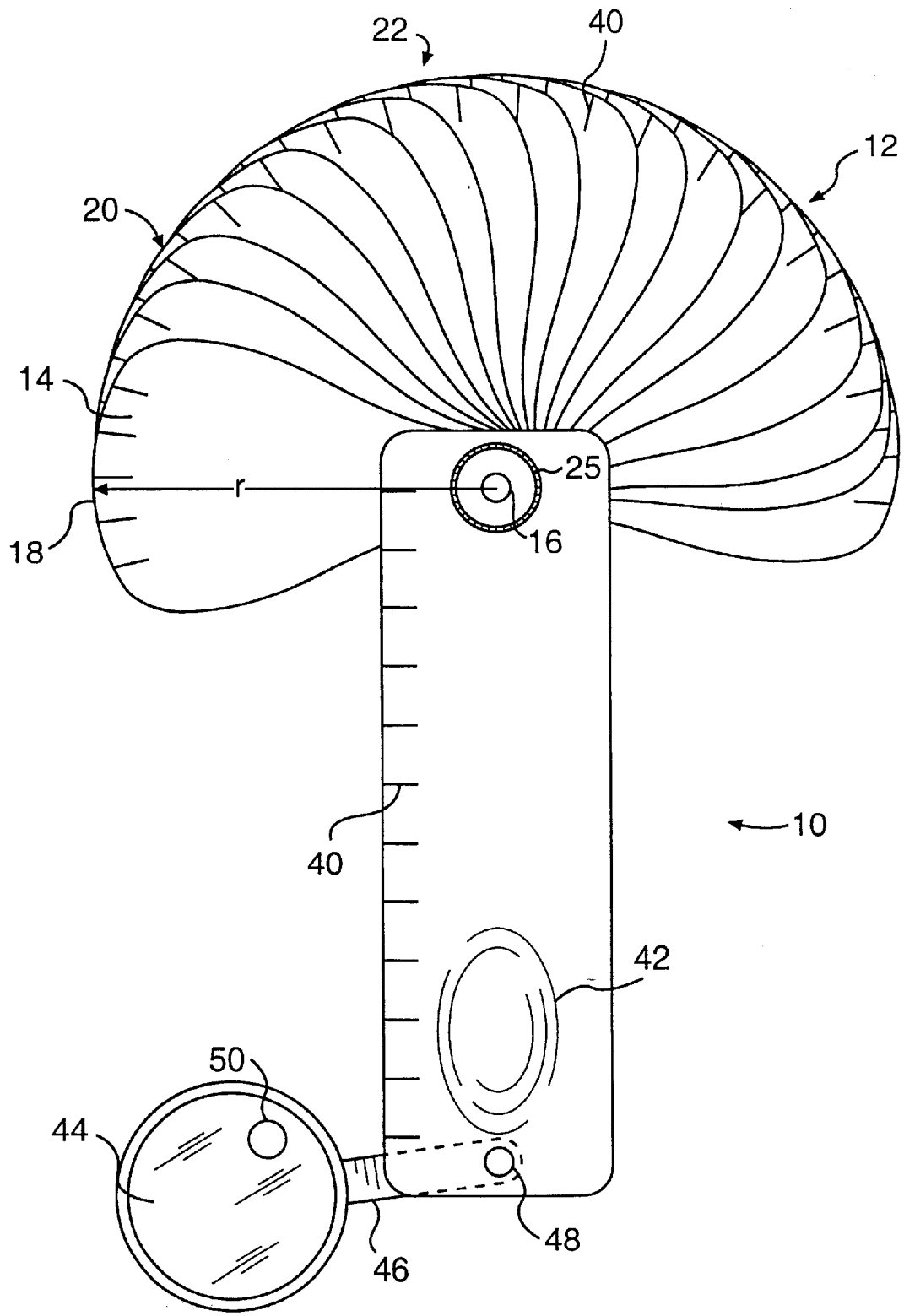
FIG. 1 is a front view of a first embodiment of the present invention showing a blocking member positioned in a use position and a magnifying glass extended from a gripping member.

Reference will now be made in detail to the presently preferred embodiments of the present invention, one or more examples of which are illustrated in the drawings. Each example is provided by way of explanation of the invention, and is not meant as a limitation of the invention. For example, features illustrated or described as part of one embodiment can be used on another embodiment to yield yet another embodiment, and it is intended that the present invention includes such modifications and variations. In the following description and in the attached figures, like or similar reference numerals will be used to identify like or similar elements.

As broadly embodied in FIGS. 1 and 2, a first embodiment of a device to assist in the reading of an illuminated image according to the present invention is designated generally by reference numeral 10. As shown, device 10 includes a blocking member 12 including a plurality of blocking portions 14. Preferably, blocking member 12 includes between three and twelve of the blocking portions 14. More preferably, blocking member 12 includes about eight of the blocking portions 14. The size and number of blocking portions are so selected as to provide a curved blocking member that is useful for blocking portions of an illuminated image, such as a mammogram, as will be discussed below.

As shown in FIG. 1, blocking portions 14 are pivotally mounted together at a common pivot point 16, which may comprise a pin, rod, screw, etc., around which blocking portions 14 may pivot. Each blocking portion 14 includes a distal end 18. The distal ends 18 of blocking portions 14 form a curved edge 20 of blocking member 12 when blocking portions 14 are in a use position 22, as shown in FIG. 1.

Blocking portions 14 may also be folded into a storage position 24, as shown in FIG. 2, for ease of storage or carrying. If desired, placing blocking portions 14 in storage position 24 may include pivoting them into a gripping member 26 to which blocking portions 14 may be mounted. In such case, gripping member 26 may be trough-shaped, and blocking portions 14 may be pivoted into storage position 24 within sides 28, 30, 32, 34, and 36 of gripping member 26. The gripping member's sides may thus define an opening 38 into which blocking portions 14 may be pivoted and stored. Side 34 may include a slot 34a to allow blocking portions 14 to pivot further out of opening 38. It should be understood that the use of a gripping member is optional, as long as the blocking portions are pivotally held together. Also, if a gripping member is used as part of the design, it is not limited to the configuration shown in the present figures. If desired, the gripping member may also be formed so as to be flexible and bendable.

As indicated in FIG. 1, markings 40 and 42 may be disposed on gripping member 26, and/or blocking member 12. The markings may be any sort suitable for facilitating measurement of portions of illuminated images, and may thus comprise, for example, a linear ruler or circular measures.

As shown in FIG. 1, curved edge 20 of blocking member 12 defines a substantially unchanging radius r along the curved edge. Each blocking portion 14 and the distal ends 18 thereof are formed substantially identical to the other, thus providing the substantially unchanging radius r. Preferably, the radius r is between about 1 and 4 inches. More preferably, the radius r is between about 2 and about 3 inches. Curved edge 20 is thus sized so as to approximate the size and shape of a portion of an illuminated image of breast tissue as will be described in more detail below.

Optionally, as also shown in FIG. 1, a magnifying glass 44 may be provided. If desired, magnifying glass 44 may be mounted to gripping member 26 via a frame 46 connected to gripping member 26 via a pivot point 48. Pivot point 48 may comprise a pin, rod, screw, etc. Preferably, magnifying glass 44 provides a magnification of about 2×. Optionally, if desired, magnifying glass 44 may include within it a spot glass 50 that may provide magnification up to 10×. As shown in FIG. 2, magnifying glass 44 may be pivoted into opening 38 in gripping member 26 for storage or carrying.

Preferably, device 10 is manufactured of lightweight materials. Thus, blocking member 12 and gripping member 26 may be made of various materials such as polyurethane, nylon, or other plastics, or steel, aluminum, or other metals. If desired, blocking member 12 may be made so as to be flexible (bendable slightly) during use, as will be described below.

Different parts of device 10 may be made relatively translucent or opaque, if so desired. Blocking member 12 should be at least partially opaque so as to be able to block illumination light during use with a backlit viewer. Also, blocking member 12 may be substantially unreflective so as to prevent glare if used with a spot viewer, rather than a backlit viewer. Optionally, blocking member 12 may include some sort of a light filter to filter certain types, wavelengths, or polarizations of light, if desired.

If desired, a mechanism may be provided for assisting in the moving of blocking portions 14 between use position 22 and storage position 24. For example, a knob 25 may be provided on the end of pivot point 16 for rotating the pivot point and/or the blocking portions. Alternately, a slide extending through gripping member 26 may cooperate with tabs on blocking portions 14 contacting slots on adjacent blocking portions to selectively extend or retract the blocking portions. Alternately, such operation could be power driven, for example via a battery and servomotor actuated by a push button. Any suitable mechanism could be utilized in this regard.

Figure 3:
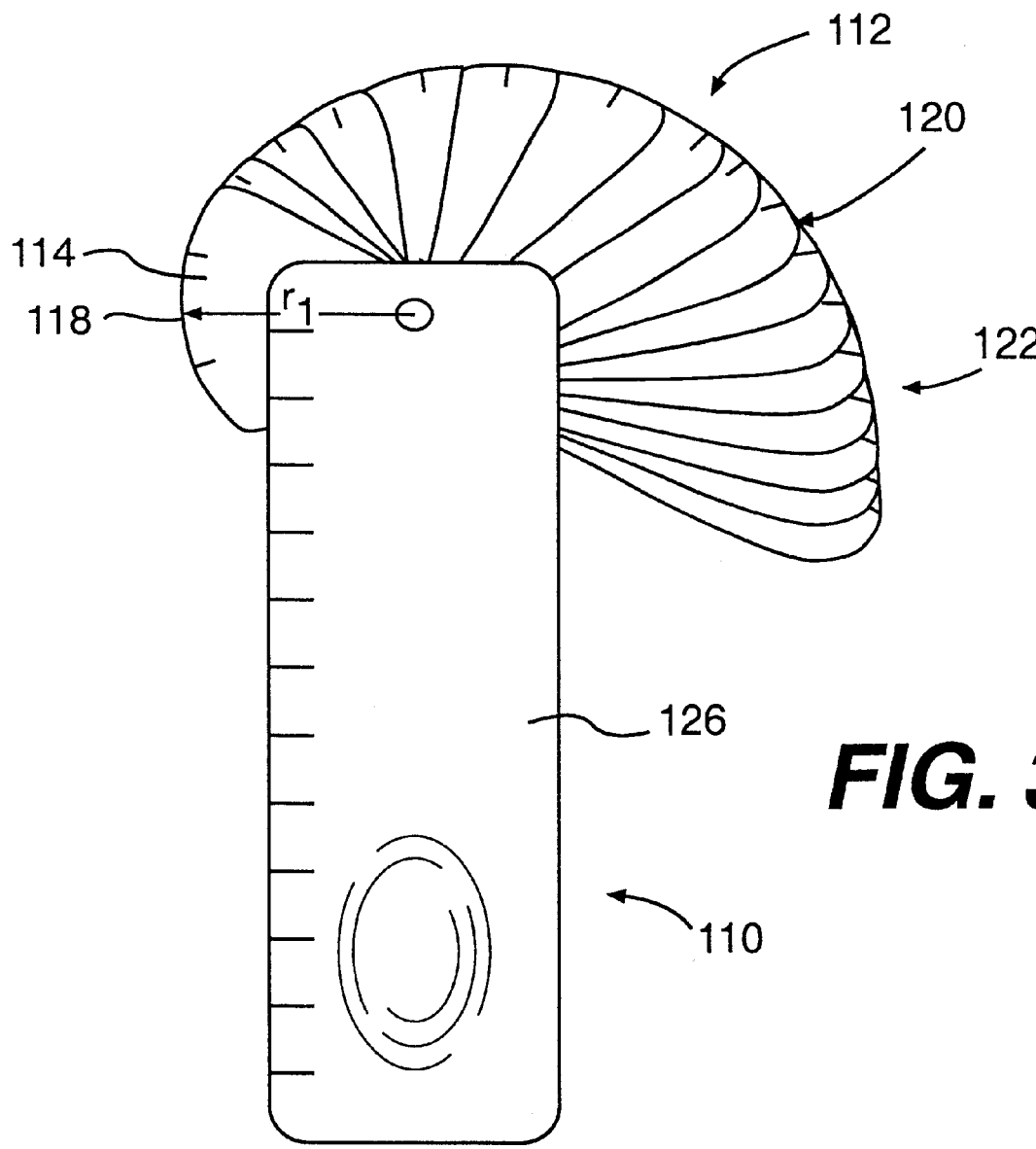
FIG. 3 is a front view of a second embodiment of the present invention showing a blocking member disposed in a use position and having a changing radius along its curved edge.

FIGS. 3 and 4 show a second embodiment of the present invention, designated by reference numeral 110, having a differing blocking member than the first embodiment. As shown in FIG. 3, blocking member 112 of device 110 includes blocking portions 114 that define a curved edge 120 when in a use position 122 different from that of device 10. Specifically, curved edge 120 defines a changing radius $r_1$ whereas curved edge 20 defines an unchanging radius r. Thus, each blocking portion 114 of device 110 includes a distal end 118 having a unique contour.

As shown in FIG. 3, radius $r_1$ changes along curved edge 120, preferably, from between at least about 1 to at most about 4 inches. The radius of curvature values set forth above allow device 110 to be used with various X-ray images in which various tissues or implants may have different curvatures. Thus, device 110 provides the potential to match up curves appearing in images more precisely, much in the way that a french curve is used by a draftsman. However, it should be understood that the changing radius is not required to practice all aspects of the present invention, as shown by device 10 in FIGS. 1 and 2.

FIG. 4 shows blocking portions 114 in a storage position 124, folded into an opening 138 within gripping member 126. FIG. 4 illustrates the differences in size between adjacent blocking portions. FIG. 4 also illustrates that different wall configurations are possible for the design of the optional gripping member.

Figure 5:
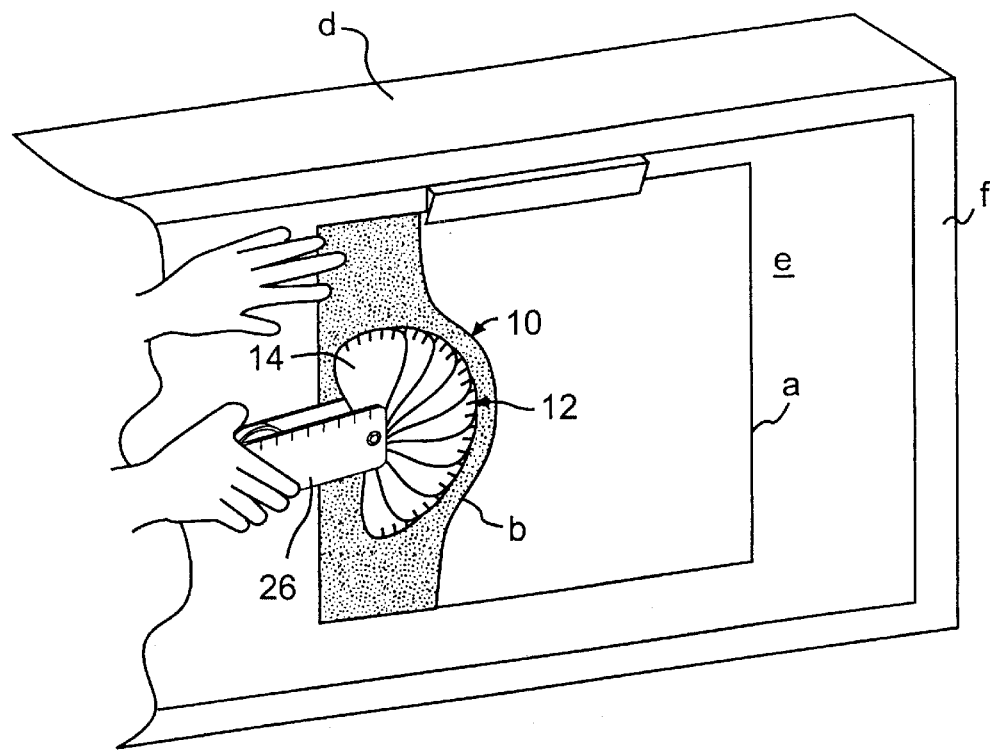
FIG. 5 is a perspective view showing use of the device of FIG. 1 to assist in reading an illuminated image.
Figure 6:
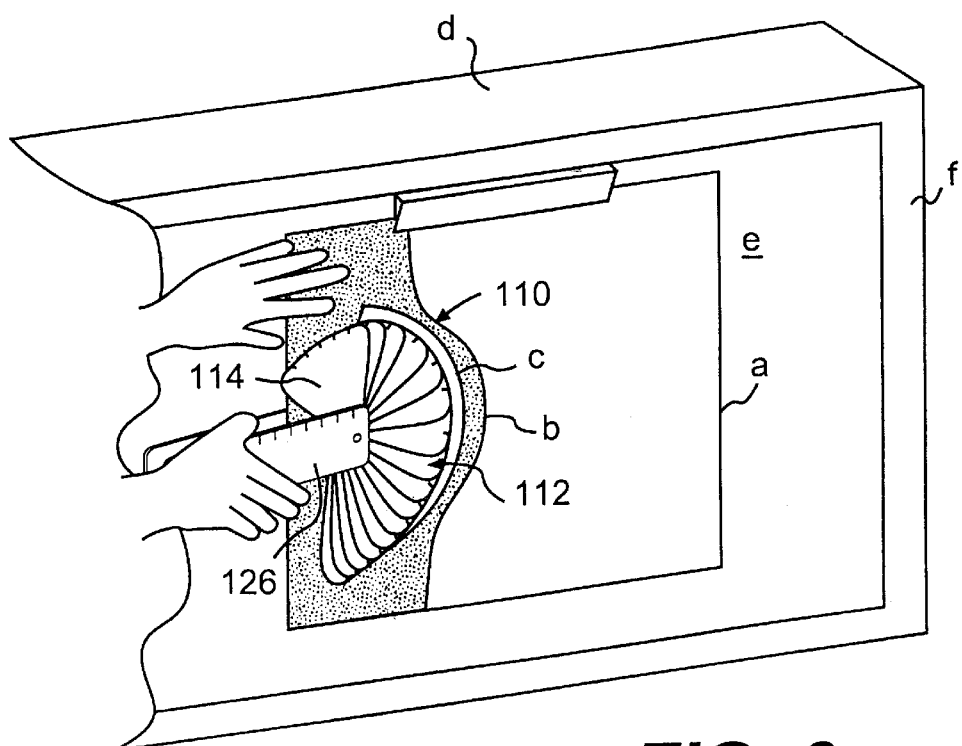
FIG. 6 is a perspective view similar to FIG. 5 wherein the illuminated image is an x-ray film image of breast tissue including a breast implant.

FIGS. 5 and 6 show devices 10 and 110 in use in reading film images. As shown in these figures, the respective blocking members 12 and 112 are extended into their use positions 22 and 122. Devices 10 and 110 are placed against X-ray images a that include breast tissue b and a breast implant c (in FIG. 6 only). X-ray image a is placed on an x-ray viewer d having a surface e supported by a frame f. The surface is backlit, and light passes through X-ray image a. Blocking members 12 and 112 block at least part of the illumination light passing from viewer d through X-ray image a to assist in reading the image. If blocking members 12 and 112 andlor gripping member 25 and 126 are made flexible, it may be easier to grip the gripping member and position the blocking member as desired.

In utilizing the devices, a physician or mammographer would illuminate the film image, for example using viewer d, pivot blocking portions 14 or 114 into the respective use position 22 or 122, place the blocking member on a portion of the illuminated film image to block at least a substantial portion of the illumination light, and then read the illuminated film image. If blocking member 12 or 112 is constructed to be entirely opaque, the physician or mammopgrapher would read portions of the image not covered by the blocking member. It is possible that the blocking member could be somewhat translucent so that the portion of the image beneath the blocking member could be read through the blocking member if desired. Also, an equivalent process could be used for reading an image displayed on a CRT or other device where film is not used.

Devices 10 and 110 thus provide for easier reading of illuminated film images, and provide particular assistance to reading of X-ray film or CRT images of breast tissue, especially images including breast implants. It will generally be apparent to those skilled in the art that various modifications and variations can be made in the present invention without departing from the scope and spirit of the invention. It is intended that the present invention include those modifications and variations as come within the scope of the appended claims and their equivalents.

I claim:

1. A device to assist in the reading of an illuminated image of breast tissue, the device comprising:

a blocking member including a plurality of blocking portions pivotally mounted together at a common pivot point so as to be pivotable between a storage position and a use position, each blocking portion having a distal end, the distal ends of the blocking portions defining a curved edge of the blocking member when the blocking portions are disposed in the use position, the blocking member being at least partially opaque for placement over a portion of the illuminated image to block at least a substantial portion of the illumination light, the curved edge being sized so as to approximate the size and shape of a portion of the illuminated image of the breast tissue.

2. The device of claim 1, wherein at least a portion of the curved edge defines a radius of curvature of between about 1 and about 4 inches.

3. The device of claim 1, wherein at least a portion of the curved edge defines a radius of between about 2 and about 3 inches.

4. The device of claim 1, wherein the curved edge defines a changing radius along the curved edge that ranges from between at least about 1 to at most about 4 inches.

5. The device of claim 1, wherein the blocking member includes between 3 and 12 of the blocking portions.

6. The device of claim 1, wherein the blocking member includes about 8 of the blocking portions.

7. The device of claim 1, farther including a gripping member, the blocking portions being pivotally mounted to the gripping member.

8. The device of claim 7, wherein the blocking portions are disposed at least partially within the gripping member when the blocking portions are in the storage position.

9. The device of claim 7, further including a magnifying glass pivotally mounted to the gripping member.

10. The device of claim 9, wherein the magnifying glass provides a magnification ratio of about 2.

11. The device of claim 1, wherein each respective distal end of the blocking portions has a common contour.

12. The device of claim 1, wherein each respective distal end of the blocking portions has a unique contour.

13. The device of claim 1, further including markings providing for measurement of portions of the illuminated images.

14. The device of claim 1, wherein the blocking member is opaque.

15. The device of claim 1, wherein the blocking member includes a light filter.

16. A device to assist in the reading of an illuminated image, the device comprising:

a gripping member, and a blocking member including a plurality of blocking portions pivotally attached to the gripping member at a common pivot point so as to be pivotable between a storage position and a use position, each blocking portion having a distal end, the distal ends of the blocking portions defining a curved edge of the blocking member when the blocking portions are disposed in the use position, the blocking member being at least partially opaque for placement over a portion of the illuminated image to block at least a substantial portion of the illumination light, the curved edge defining a changing radius along the curved edge that ranges from between at least about 1 to at most about 4 inches.

17. The device of claim 16, wherein the blocking member includes between 3 and 12 of the blocking portions.

18. The device of claim 16, wherein the blocking member includes about 8 of the blocking portions.

19. The device of claim 16, wherein the blocking portions are disposed at least partially within the gripping member when the blocking portions are in the storage position.

20. A method of reading an illuminated image of breast tissue, the method comprising:

illuminating an image of breast tissue;

pivoting a plurality of blocking portions of a blocking member into a use position, the blocking portions being pivotally mounted together at a common pivot point so as to be pivotable between a storage position and the use position, each blocking portion having a distal end, the distal ends of the blocking portions defining a curved edge of the blocking member when the blocking portions are in the use position, the curved edge being sized so as to approximate the size and shape of a portion of the illuminated image;

placing the blocking member on a portion of the illuminated image to block at least a substantial portion of the illumination light; and reading the illuminated image.

21. The method of claim 20, wherein the curved edge of the blocking member defines a changing radius of curvature along the curved edge that ranges from between at least about 1 to at most about 4 inches.

22. The method of claim 20, wherein the pivoting step includes the sub-step of pivoting the plurality of blocking portions out of a gripping member.

* * * * *